United States Patent [19]

Fredrick

[11] Patent Number: 4,675,327

[45] Date of Patent: Jun. 23, 1987

[54] ANTI-MICROBIAL COMPOSITIONS

[75] Inventor: Jerome F. Fredrick, Bronx, N.Y.

[73] Assignee: The Dodge Chemical Company, Cambridge, Mass.

[21] Appl. No.: 483,281

[22] Filed: Apr. 8, 1983

Related U.S. Application Data

[63] Continuation of Ser. No. 786,460, Apr. 11, 1977, abandoned.

[51] Int. Cl.$^4$ ..................... A01N 43/40; A01N 31/08; A01N 37/10; A01N 35/02
[52] U.S. Cl. .................................... 514/383; 514/419; 514/459; 514/569; 514/694; 514/695; 514/736
[58] Field of Search ............... 424/75, 269, 334; 71/3; 514/383, 419, 459, 569, 694, 695, 736

[56] References Cited

U.S. PATENT DOCUMENTS

| | | | |
|---|---|---|---|
| 814,775 | 3/1906 | Dodge | 424/75 |
| 1,495,196 | 5/1924 | Oakley | 424/75 |
| 2,318,733 | 5/1943 | Avery | 47/58 |
| 2,333,182 | 11/1943 | Jones | 424/75 |
| 2,918,402 | 12/1959 | Fredrick | 424/75 |
| 2,945,322 | 7/1960 | Gaeth et al. | 47/9 |
| 3,000,782 | 9/1961 | Landau et al. | 424/75 |
| 3,057,775 | 10/1962 | Rendon | 424/75 |
| 3,202,574 | 8/1965 | Berliner | 424/75 |
| 3,336,129 | 8/1967 | Herrett et al. | 71/92 |
| 3,444,162 | 5/1969 | Hyatt | 260/240 |
| 3,821,216 | 6/1974 | Domenico | 424/75 |

FOREIGN PATENT DOCUMENTS 1148706  5/1963  Fed. Rep. of Germany ........ 424/75

OTHER PUBLICATIONS

Frear-Chemistry of the Pesticides, 3rd. Ed.-(1955), D. Van Nostrand, Co., N.Y., pp. 394–396.
Crafts, "The Chemistry & Mode of Action of Herbicides"—Interscience Publ., N.Y.—pp. 10, 48–50, 162, 223–224, 238–245 & 263—1962.
Chem. Abst. 57, 10194(b) (1962).

*Primary Examiner*—Douglas W. Robinson
*Attorney, Agent, or Firm*—David G. Conlin; Gregory D. Williams

[57] ABSTRACT

Embalming preparations, which are far less noxious than previously known compositions, comprise a combination of a disinfectant and a plant growth regulating compound. The compositions achieve anti-microbial potency at concentrations of these ingredients far lower than the concentration levels of disinfectants found in known embalming preparations.

13 Claims, No Drawings

ANTI-MICROBIAL COMPOSITIONS

The present application is a continuation application of U.S. patent application Ser. No. 786,460, filed Apr. 11, 1977, now abandoned.

BACKGROUND OF THE INVENTION

This invention relates to embalming fluids containing anti-microbial agents, in particular to embalming fluids containing combinations of both disinfectants and plant growth regulators, which combinations exhibit high anti-microbial effect with but small concentrations of ingredients.

Embalming fluids are well known and described in the art. Typical formulations used for embalming fluids are disclosed in Frederick and Strubb, *Principles and Practice of Embalming*, pages 199–220 (4th ed. 1967), and Mendelsohn, *Embalming Fluids*, Chapter 4 (Chemical Publishing Co., NY 1940), both of which are hereby incorporated by reference.

As is known in the art, embalming fluids are employed for the purpose of disinfecting and preserving the dead human body and for creating and maintaining a natural appearance. There are three general types of embalming fluids, identified as arterial fluids, pre-injection fluids, and cavity fluids. Many embalming fluids essentially contain aqueous solutions of formaldehyde in varying strength, with other additives to produce desired results. For example, in arterial fluids, it is common to find anti-coagulants to inhibit or retard blood clotting, chemicals such as various buffer pairs to control and vary pH and toxicity, relaxing agents to relax muscle tissue, various inorganic salts to control specific gravity, hardening power, and various other properties of the fluid, surface active agents, dyes, and the like.

Disinfectants are included in embalming fluids in order to kill or destroy disease-causing microorganisms, including both bacteria and fungi. Both groups of microorganisms can be "killed" (their metabolic processes disrupted) by a wide class of biocidally-active chemicals termed "disinfectants". The use of such disinfectants in the process of embalming is of highest importance, since that process has for its goal not only the preservation of the physical body for psychological value to the bereaved, but most importantly the thorough disinfection of the cadaver so that it does not present a public health hazard.

While both aims of professional embalming are achieved by the use of commercially available embalming fluids, such fluids are sold as concentrates containing high concentrations of the components. The use of these concentrates results in high levels of fumes, which not only make the fluids unpleasant to work with, but are often toxic and may indeed present an occupational hazard for the professional embalmer or other mortuary personnel.

Accordingly, it is an object of the present invention to provide an improved embalming fluid exhibiting increased disinfectant or anti-microbial effects. It is a further object to provide embalming fluids which exhibit anti-microbial effects which are as good as known embalming fluids, while requiring far less disinfectant for the irradication of microorganisms, substantially without production of the noxious fumes produced by those known embalming fluids.

These and other objects are accomplished by the embalming fluid compositions of the present invention, which contain, in addition to a disinfectant, certain amounts of chemicals known commercially as "plant growth regulators". It has now been found that combinations of the chemical substances known as disinfectants and the chemical substances known as plant growth regulators results in a synergistic improvement in bringing about the death of bacteria and fungi.

Disinfectants are materials which destroy or inhibit the microorganisms causing disease. A wide variety of disinfectants are suitable for use in accordance with the present invention. Such agents include anti-bacterial agents such as sulfonamides, isoniazid, p-amino salicylic acid, penicillin and its derivatives, e.g. penicillin V, unpenicillin, cephalosporin and its derivatives, e.g. well-known compounds of the structures of cephalosporin A, cephalosporin C, e.g. cephaloridine, cephalothin, etc., streptomycin, tetracyclines, chloramphenicols, erythromycin, novobiocin, neomycin, bacitracin, polymyxin, etc., and salts thereof; anti-fungal agents such as griseofulvin, nystatin, etc., and salts thereof; plant chemotherapeutics such as captan (N-trichlorothiotetrahydrophthalimide), maneb (manganese ethylene bisdithiocarbamate), thiram (tetramethylthiuram disulfide); known skin disinfectants such as alcohols, particularly lower alkyl alcohols, e.g. methanol, ethanol, isoproponal, etc.; sources of active halogens (fluorine, chlorine, bromine or iodine), e.g. solutions of halogens, salts such as sodium hypochlorite, iodophors (surface active detergents containing iodine as part of the molecule), etc.; phenolics, e.g. phenol, cresol, and their derivatives, particularly the halogenated alkylated and/or nitrated derivatives, such as o-phenylphenol, hexachlorophene, p-chloro-m-cresol, bithionol, etc.; aldehydes, e.g. formaldehyde, glyoxal, gluteraldehyde, succinaldehyde, etc., particularly lower alkyl aldehydes; peracids and derivatives thereof, e.g. peracetic acid, perpropionic acid, perbutyric acid, perbenzoic acid, preferably lower alkyl peracids; quaternary ammonium compounds, which are cationic detergents and derivatives having nitrogen with a quaternary valence, e.g. ammonium((5-hydroxy-4-oxo-4H-pyran-2-yl)methyl)-dimethyl tetradecyl chloride (hereinafter referred to as ADAK), and others, e.g. disclosed in my U.S. Pat. No. 2,918,402, incorporated herein by reference; metal binding agents, including chelating compounds and sequestering compounds, e.g. 8-hydroxyquinoline (or oxine), ethylene diamine tetraacetic acid, nitrilotriacetic acid, and others well known in the art; and numerous dyes; e.g. acridine dyes, gentian violet, and many others well known in the art. Other disinfectants include heavy metal disinfectants such as mercurial compounds, e.g. mercuric bichloride, mercuric oxycyanide, potassium mercuric iodide, organic mercurials such as phenylmercuric; silver compounds, e.g. silver nitrate, ammoniacal silver nitrate, silver picrate, etc., copper compounds, arsenic compounds, etc. However, while the heavy metal compounds are efficient disinfectants, their use in embalming fluids is prohibited by law in many areas, primarily for environmental reasons. Many other suitable disinfectants will be readily apparent to the skilled in the art. Presently preferred are formaldehyde and the quaternary ammonium compounds, as well as the other known disinfectants used in embalming, such as the sodium derivative of o-phenylphenol, p-chloro-m-cresol, tribromothymol, glyoxal, glutaraldehyde, etc.

Suitable plant growth regulators include naturally occurring plant growth regulators including the "auxins," e.g. auxentiolic acid, auxenolonic acid, β-indolylacetic acid or salts of such acids, indole-3-acetonitrile, etc., as well as the gibberelic acids and salts therof and the kinins, and others known in the art; synthetic agents based on the molecular structure of the natural agents (aka "synthetic auxins"), e.g. α-(indole-3)-propionic acid, γ-(indole-3)-butyric acid, etc.; substituted phenols, e.g. 2-sec butyl-4, 6-dinitrophenol (dinoseb or DNBP), 2-(1-methylbutyl)-4, 6-dinitrophenol (dinosam or DNAP), pentachlorophenol (PCP); chlorophenoxy compounds, e.g. (2,4-dichlorophenoxy)acetic acid (2,4-D), (2,4,5-trichlorophenoxy)acetic acid (2,4,5-T), ((4-chloro-O-tolyl)oxy)acetic acid (MCPA), 4-((4-chloro-O-tolyl)oxy)butyric acid (MCPB); chloro-substituted or methyl-substituted acetic and propionic acids and salts thereof, e.g. trichloroacetic acid, amides such as N,N-diallyl-2-chloroacetamide (CDAA), 2-chloro-N,N-diethylacetamide (CDEA), 1,2-dihydro-5,6-pyridazine dione (MH); ureas, e.g. 1,3-bis(2,2,2-trichloro-1-hydroxyethyl)urea (DCU), 1,1-dimethyl-3-phenylurea (fenuron), 3-(3,4-dichlorophenyl)-1,1-dimethylurea (diuron), 3-(p-chlorophenyl)-1,1-dimethylurea (monuron), 1-butyl-3-(3,4-dichlorophenyl)-1-methylurea (reburon); carbamates, such as 4-chloro-21-butynyl-m-chlorocarbanilate, butyn-1-yl-N-3-chlorophenylcarbamate-N-(3-chlorophenyl)carbamate; thiocarbamates, e.g. s-ethyl dipropylthiocarbamate (EPTC), s-(2,3-dichloroallyl)-diisopropylthiocarbamate (Diallate); dithiocarbamates, e.g. 2-chloroallyl diethyldithiocarbamate (CDEC), sodium methyldithiocarbamate (Metham), thiodiazines, e.g. tetrahydro-3,5-dimethyl-2H-1,3,5-thiadiazene-2-thione (dazomet); triazoles, e.g. 3-amino-s-triazole (amitrole); triazines, e.g. 2-chloro-4,6-bis(ethylamino)-s-triazine (simazine), 2-chloro-4,6-bis(diethylamino)-s-triazine (chlorazine), 2-chloro-4-(diethylamino)-6-(ethylamino-s-triazine (trietazine), ipazine, atrazine, simetone, prometone, atratone, etc.; benzoic acids, e.g. 2,3,6-trichlorobenzoic acid (2,3,6-TBA), chlorinated benzoic acid (PB), amiben, nitroben, etc.; chlorinated benzenes, e.g. dichlorobenzene, trichlorobenzene; and other known regulators, e.g. NPA, (acetato) phenyl mercury (PMA), potassium cyanide, 1,1,1,3,3,3-hexachloro-2-propanone (HCA), IPX, OCH, O,O-diethyl dithio bis (thioformate) (EXD), methanearsonic acid (MAA), EBEP, DIPA, DMA, ammonium sulfamate (AMS), ferac, endothal, diquat, acrolein maleic hydrazide. Others are known in the art. See, e.g. Ashton and Crafts, *Mode of Action of Herbicides* (N.Y. 1973), incorporated herein by reference, particularly Chapter 13, for carbamates and Chapters 16–22 for phenols, phenoxys, thiocarbamates, triazines, triazoles, ureas, and unclassified compounds, respectively. Particularly preferred are amitrol, beta-indolyl acetic acid, and alphanaphthyl acetic acid.

Accordingly, it has now been found that arterial and cavity embalming fluids, as well as many adjunct and accessory chemicals used in embalming, can be formulated which will be much less toxic in cases of contact or accidental ingestion, and which are much more pleasant to the embalmer to work with, because of the lack of noxious fumes. It has been discovered that by using these synergistic combinations of plant growth regulators and disinfectants, it is possible to reduce the concentration of toxic chemicals substantially, and yet achieve identical biological results on bacteria and fungi as those produced by the more highly concentrated, toxic fluids that do not contain the synergistic combination.

The amounts of the growth regulators and disinfectants to be included in the embalming and other fluids made in accordance with the present invention, depends on a number of factors. Basically, the combination of plant growth regulator and disinfectant should be present in an amount which is sufficient to at least stop the reproduction of the microorganisms with which it will come in contact in the body, but should not be present in such high concentrations as to give off noxious fumes. While reproduction-arresting, e.g. bacteriostatic, amounts of these ingredients are sufficient to eradicate infection by the normal death rate of the non-reproducing microorganisms, preferably the growth regulator and disinfectant are present in sufficient amounts to act as a microbicide, e.g. a bacteriocidal-agent, which kills the microorganisms directly. Preferably, the concentrations of each of the plant growth regulator and the disinfectant in the embalming fluid are less than their lethal dosage, should accidental ingestion of the fluid take place. Within these broad ranges, the total concentration of the combination of growth regulator and disinfectant may vary considerably. Because of increase in effectiveness achieved through the combination, concentrations of the ingredients as low as a few parts per million may still be effective against bacteria and fungi. Preferably the concentration of each of these two ingredients is at least about ten parts per million, more preferably at least about 40 parts per million. The preferred concentration of the total of both ingredients if from 0.0001% to 0.1% by weight, preferably from 0.0005% to 0.015% by weight, most preferably from 0.001% to 0.01% by weight. The ratio of plant growth regulator to disinfectant used in the combination may vary from 100:1 to 1:100, but preferably is within the range of 10:1 to 1:10, and most preferably is from about 5:1 to about 1:5.

Where one of the components is present in the fluid for more than one purpose, it should be included in a concentration which would be sufficient to satisfy all of its intended functions. For example, most preservative chemicals have for goals in embalming both the fixation of proteins and other elements of the cadaver, and the disinfection of the tissues of the cadaver. By formulating a synergistic combination into an arterial fluid or cavity fluid, the enhanced germicidal action has a "sparing" action on the formaldehyde or other preservative chemical component which is designed to fix protein. In other words, while it was previously necessary to include large amounts of such compounds in order to satisfy both the disinfecting and protein fixation functions, as a result of the present invention, the amount of such compounds necessary in the formulation is substantially reduced, since the amount necessary to satisfy the disinfecting function is vastly reduced. This makes a larger amount of such compounds available for the fixation of protein. It thus becomes feasible to formulate an arterial or cavity fluid with a minimum actual concentration of formaldehyde with a small amount of a plant growth regulating compound, which fluid will be as effective in its action as known fluids containing much higher formaldehyde concentrations.

The anti-microbial effect of the compositions of the present invention on both fungi and bacteria is demonstrated by consideration of the following illustrative embodiments:

EXAMPLE I

The microbial action of aqueous solutions of varying concentrations of amitrol and a quaternary ammonium disinfectant ammonium((5-hydroxy-4-oxo-4H-pyran-2-yl)methyl)dimethyl tetradecyl chloride (hereinafter referred to as ADAK), against the fungus *P. notatum*. Growths of *P. notatum* on standard nutrient media were treated with samples of the solutions listed below, and the zone of inhibition (hereinafter noted as ZI) was measured as per the A.O.A.C. procedures. The following results were obtained:

| AMITROL | ADAK   | ZI (mm) |
| ------- | ------ | ------- |
| 0.005 M | 0.000  | 7.2     |
| 0.000   | 0.005% | 6.5     |
| 0.010 M | 0.000  | 12.0    |
| 0.000   | 0.010% | 14.5    |
| 0.005 M | 0.005% | 32.0    |

EXAMPLE II

The same procedure was followed in evaluating aqueous combinations of the plant growth regulator amitrol and the disinfectant formaldehyde ($CH_2O$) against the bacterium *B. subtilis*:

| AMITROL | $CH_2O$ | ZI (mm) |
| ------- | ------- | ------- |
| 0.005 M | 0.000   | 8.0     |
| 0.000   | 0.001%  | 9.0     |
| 0.010 M | 0.000   | 12.0    |
| 0.000   | 0.002%  | 16.5    |
| 0.005 M | 0.001%  | 36.0    |

EXAMPLE III

Using the same technique, the aqueous solutions of the plant growth regulator amintrol and the disinfectant ortho-phenyl phenol (OPP) are tested against the fungi *P. notatum*:

| AMITROL | OPP     | ZI (mm) |
| ------- | ------- | ------- |
| 0.005 M | 0.000   | 6.5     |
| 0.000   | 0.001 M | 12.0    |
| 0.010 M | 0.000   | 11.0    |
| 0.000   | 0.002 M | 20.5    |
| 0.005 M | 0.001 M | 30.5    |

EXAMPLE IV

Using the same techniques, aqueous solutions of amitrole and ADAK were tested against the bacteria *B. subtilis*, giving the following results:

| AMITROL | ADAK   | ZI (mm) |
| ------- | ------ | ------- |
| 0.005 M | 0.000  | 8.0     |
| 0.000   | 0.005% | 7.5     |
| 0.010 M | 0.000  | 12.0    |
| 0.000   | 0.010% | 10.5    |
| 0.005 M | 0.005% | 27.5    |

EXAMPLE V

Using the same techniques, aqueous solutions of the plant growth regulator β-indolyl acetic acid (sodium salt) (hereinafter IAA) and of the disinfectant ADAK were tested against the bacteria *S. aureus*. The following results were obtained:

| IAA     | ADAK   | ZI (mm) |
| ------- | ------ | ------- |
| 0.001 M | 0.000  | 5.0     |
| 0.000   | 0.005% | 7.0     |
| 0.002 M | 0.000  | 9.5     |
| 0.000   | 0.010% | 11.0    |
| 0.001 M | 0.005% | 27.0    |

EXAMPLE VI

Using the same techniques, aqueous solutions of the plant growth regulator α-naphthyl acetic acid (sodium salt) (hereinafter NAA) and the disinfectant formaldehyde were tested against the mold *A. niger*, giving the following results:

| NAA     | $CH_2O$ | ZI (mm) |
| ------- | ------- | ------- |
| 0.001 M | 0.000   | 10.0    |
| 0.000   | 0.001%  | 9.0     |
| 0.002 M | 0.000   | 14.0    |
| 0.000   | 0.002%  | 12.5    |
| 0.001 M | 0.001%  | 35.5    |

An example of a low concentration disinfectant containing low concentrations of the toxic ingredients would contain 25 mg of ADAK and 200 mg of amitrol per standard 16 ounce embalming chemical bottle, giving 420 parts per million of amitrol and 50 parts per million of ADAK. The lethal dosage of amitole is given by *Merck Index*, 8th edition, page 63 (1968) as 14.7 grams per kilogram. The lethal dose of ADAK is given by *The National Cancer Institute Screening Reports*, NSC-68957D, as 125 mg/kg. Accordingly, the concentrations of this synergistic combination in this disinfectant could still be increased four to five times and still remain well below the toxic levels.

The embodiments of this invention which have been described and illustrated are intended to be exemplary only, and many modifications will be apparent to those skilled in the art from a consideration of this disclosure, or from a practice of this invention. All of these modifications and advantages are considered and intended to be within the scope and the spirit of the appended claims.

I claim:

1. An antimicrobial composition, comprising a first component selected from formaldehyde, ammonium((5-hydroxy-4-oxo-4H-pyran-2-yl)methyl)dimethyl tetradecyl chloride, and o-phenylphenol, and a second component selected from amitrol, β-indolyl acetic acid and alpha-naphthyl acetic acid.

2. The composition of claim 1, wherein the first component comprises formaldehyde.

3. The composition of claim 1, in which the first component comprises ammonium((5-hydroxy-4-oxo-4H-pyran-2-yl)methyl)dimethyl tetradecyl chloride.

4. The composition of claim 1, wherein the second component is amitrol.

5. The composition of claim 1, wherein the second component is β-indolyl acetic acid.

6. The composition of claim 1, wherein the second component is alpha-napthyl acetic acid.

7. The composition of claim 1, wherein the first component is formaldehyde, and the second component is amitrol.

8. The composition of claim 7, wherein the total concentration of amitrol and formaldehyde ranges is between about 0.0001 to about 0.1 percent by weight.

9. The composition of claim 8, wherein said total concentration is from about 0.001 to about 0.01 percent by weight.

10. The composition of claim 7, wherein the ratio of formaldehyde to amitrol is between about 1:10 and 10:1.

11. The composition of claim 7, wherein the ratio of amitrol to formaldehyde is between about 1:5 and 5:1.

12. An antimicrobial composition, comprising formaldehyde and amitrol, wherein the total concentration of formaldehyde and amitrol is between about 0.0001 to about 0.1 percent by weight and the ratio of formaldehyde to amitrol is between about 10:1 to about 1:10.

13. An antimicrobial composition comprising formaldehyde and amitrol, wherein the concentration of formaldehyde is 0.001 percent by weight and the concentration of amitrol is 0.005M.

* * * * *